LILAC PLANT

Filed June 15. 1973 2 Sheets-Sheet 1

United States Patent

Plant Pat. 3,694

Patented Mar. 25, 1975

3,694

LILAC PLANT

Leonard K. Slater, Agincourt, Ontario, Canada, assignor of a fractional part interest to Sheridan Nurseries Ltd.

Filed June 15, 1973, Ser. No. 370,463

Int. Cl. A01h *5/00*

U.S. Cl. Plt.—66 1 Claim

This invention relates to a new and distinct variety of lilac plant, and particularly to a hybrid French Lilac *Syringa vulgaris.*

The new variety is a cross of the well known *Syringa vulgaris* hybrid "Frank Patterson" with another well known *Syringa vulgaris* hybrid "Dr. Brethour"; both of those varieties being well know cultivars which are maintained by Sheridan Nurseries Ltd., of 700 Evans Avenue, Etobicoke, Ontario M9C 1A3, Canada.

The present variety is distinguished from other French Lilac plants in that it has a compact growth habit—about six feet high in eleven years, with discernible growth having ceased, and being well rounded. In addition, the new variety exhibits large flowers with much darker purple colour than its parent *Syringa vulgaris* "Frank Patterson," and with earlier blooming than that parent. The flowers of the present variety are heavily scented.

The new variety first flowered in 1957, and was evaluated in a population of about 200 seedlings of the cross *Syringa vulgaris* "Frank Patterson" × *Syringa vulgaris* "Dr. Brethour," noted above, about five years from seed. At that time, the seedling was about three feet high, and was noted as having the largest and darkest flowers. The new variety was isolated, and first grafts were taken in 1963.

Since March 1968, grafts have been made on *Syringa villosa* understock at the nursery of Sheridan Nurseries Ltd. at 1116 Winston Churchill Boulevard, Oakville, Ontario; and this asexual reproduction has proven the characteristics of the new variety as being true.

Figure 1:
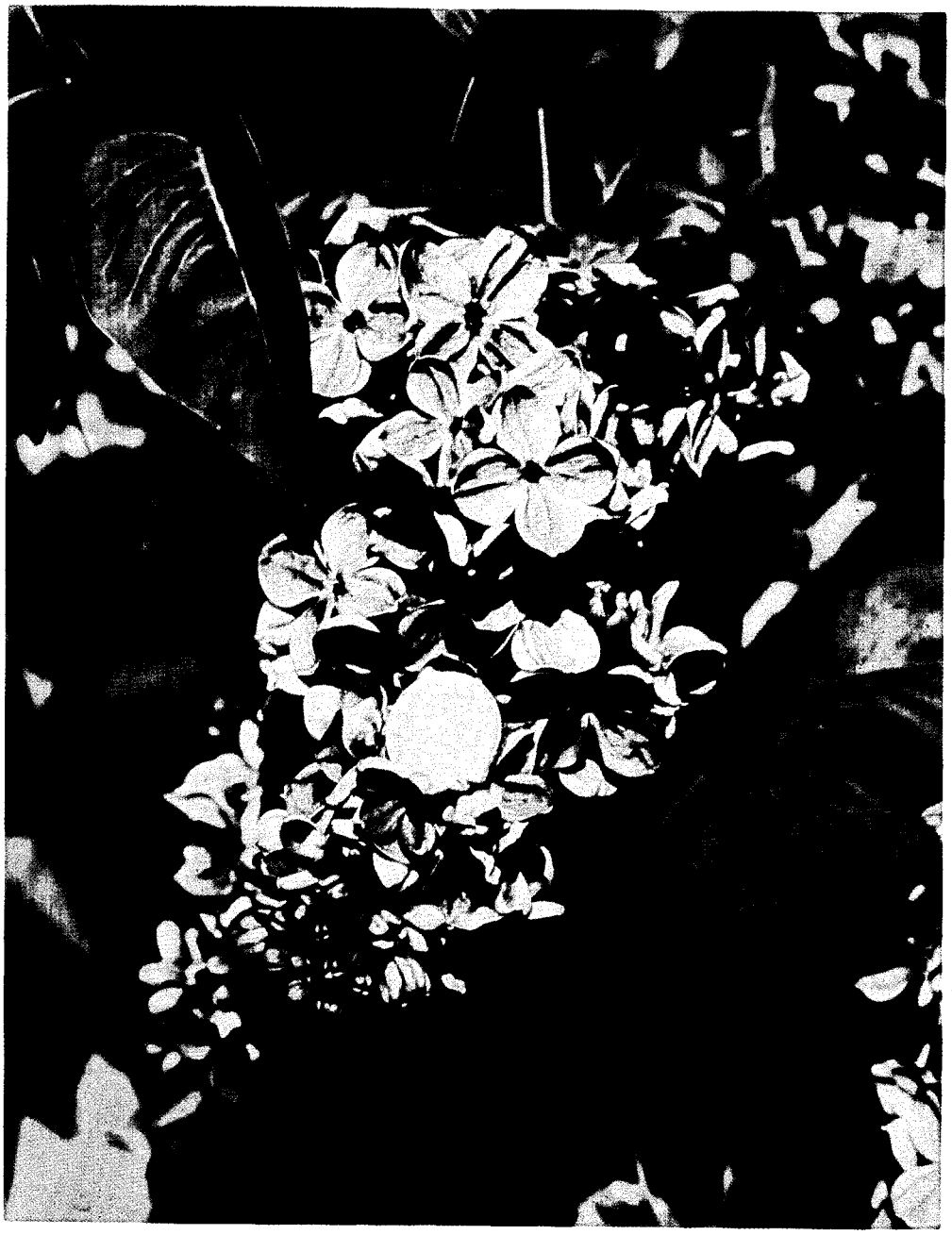
Figure 2:
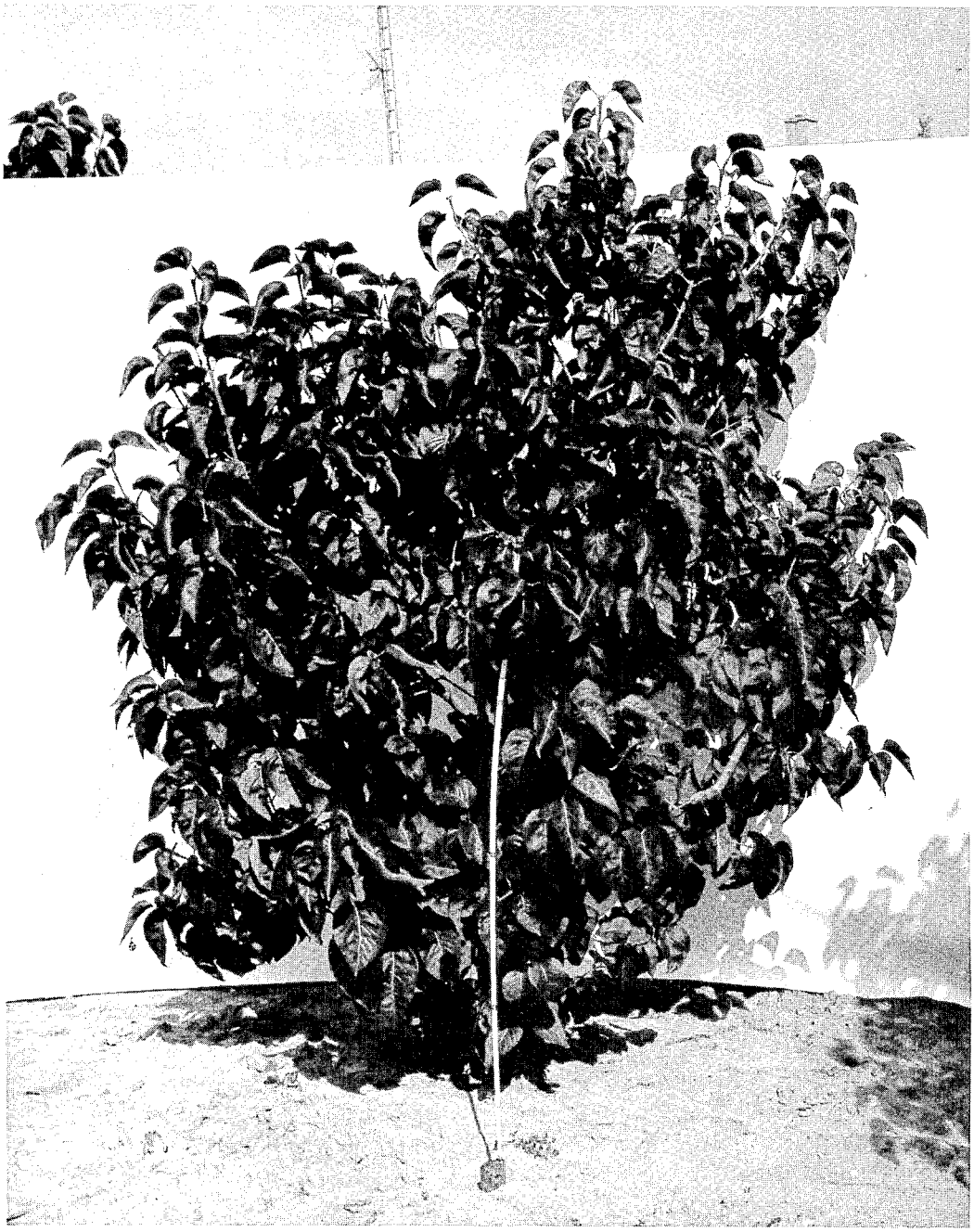

More detailed description of the present variety follows, taken together with the accompanying drawings, of which:

FIG. 1 is a colour photograph, showing as well as possible by this method of illustration, the shape and colour of a flower spike of a mature plant according to this invention; and FIG. 2 is a black and white photograph illustrating the growth habit of the present variety.

THE PLANT

Type: French Lilac *Syringa vulgaris.*

Breeding: Hybrid.

Parentage: *Syringa vulgaris* "Frank Patterson" × *Syringa vulgaris* "Dr. Brethour."

Growth habit: Compact growth habit, to about six feet high in eleven years; well rounded; further growth in height apparently having ceased. The branches are slender, coloured brown as is usual in French Lilac hybrid plants, with no lenticels.

Foliage: Numerous leaves, green, heart-shaped, about three inches long by one and one-half inches wide; medium thickness; smooth edge; medium petiole; and no glands.

Flower buds: Hardy; panicle-shaped; deep purple coloured. The panicle is about 10 inches long, and its greatest width is about 8.5 inches. There are about 385 florets per panicle.

Flowers: Abundant flowers, first blooming about May 20 in the Toronto region, with full bloom about June 1. The flowers are large. The colour is deep purple-red, typically No. 5RP3/9 with reference to the Nickerson Colour Fan published by Munsell Color Company, Incorporated, of Baltimore, Md. In each floret there are five petals, incurved and slightly cupped at the edges, each about one inch across.

Fruit: Not abundant.

I claim:

1. A new and distinct variety of *Syringa vulgaris* hybrid French Lilac plant, characterized in that the mature plant is about six feet high, well rounded; and in that its flowers are large, with large florets, and of a deep purple-red colour.

No references cited.

ROBERT E. BAGWILL, Primary Examiner